(12) United States Patent
Honda et al.

(10) Patent No.: US 6,838,567 B1
(45) Date of Patent: Jan. 4, 2005

(54) PROCESS FOR PRODUCING OPTICALLY ACTIVE AZETIDINE-2-CARBOXYLIC ACIDS

(75) Inventors: Tatsuya Honda, Kobe (JP); Nobuo Nagashima, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/959,980

(22) PCT Filed: May 15, 2000

(86) PCT No.: PCT/JP00/03079

§ 371 (c)(1),
(2), (4) Date: Apr. 19, 2002

(87) PCT Pub. No.: WO00/69817

PCT Pub. Date: Nov. 23, 2000

(30) Foreign Application Priority Data

| May 21, 1999 | (JP) | ............................................. | 11/142271 |
| May 14, 1999 | (JP) | ............................................. | 11/134736 |
| Jun. 16, 1999 | (JP) | ............................................. | 11/169620 |

(51) Int. Cl.$^7$ .................... C07D 207/12; C07D 205/00; C07C 229/00
(52) U.S. Cl. ......................... 548/543; 548/950; 562/574
(58) Field of Search ................................ 548/541, 543, 548/544, 950; 562/456, 574

(56) References Cited

FOREIGN PATENT DOCUMENTS

| EP | 257602 A1 | 8/1987 |
| EP | 393441 A1 | 10/1990 |
| EP | 844242 A1 | 5/1998 |
| EP | 855446 A2 | 7/1998 |
| JP | 48-052721 A | 7/1973 |
| JP | 49-11844 A | 2/1974 |
| JP | 49-054532 A | 5/1974 |
| JP | 60-120888 A | 6/1985 |
| JP | 61-085392 A | 4/1986 |
| JP | 63-060954 A | 3/1988 |
| JP | 04-095067 A | 3/1992 |
| JP | 08-119935 A | 5/1996 |

OTHER PUBLICATIONS

Yamada et al, Agricultural and Biological Chemistry, Synthesis of (+–)–Azetidine–2–carboxylic Acid and 2–Pyrrolidone Derivatives, 1973, 37(3), pp. 649–652.*

J. Med. Chem., 1997, vol. 30, No. 11, pp. 1995–1998.

J. Med. Chem., 1996, vol. 39, No. 4, pp. 817–825.

J. Antibiol., 1990, vol. 43, No. 7., pp. 858–872.

* cited by examiner

*Primary Examiner*—Paul A. Zucker
(74) *Attorney, Agent, or Firm*—Kenyon & Kenyon

(57) ABSTRACT

An optically active N-protected azetidine-2-carboxylic acid (5) can be produced by preparing an optically active 4-amino-2-halobutyric acid (3)

- by halogenating an optically active 3-hydroxy-2-pyrrolidinone (1) with inversion of configuration to prepare an optically active 3-halo-2-pyrrolidinone (2) followed by hydrolysis or
- by halogenating an optically active 4-amino-2-hydroxybutyric acid ester (6) with inversion of configuration to prepare an optically active 4-amino-2-halobutyric acid ester (7) followed by hydrolysis or
- by halogenating the compound (6) with inversion of configuration to prepare the compound (7), cyclizing the same to prepare the compound (2) followed by hydrolysis, further cyclizing the compound (3) followed by treating the reaction product with an amino group-protecting agent. The thus-obtained compound (5) can be improved its optical purity further by recrystallization

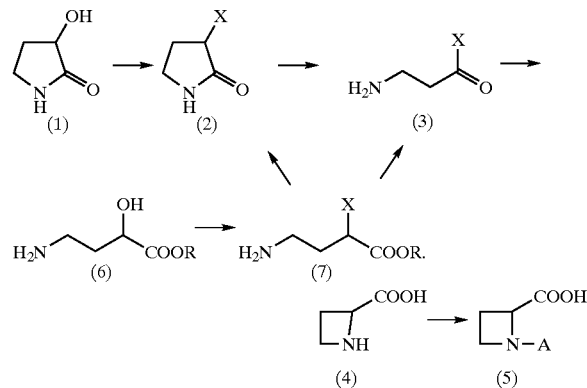

32 Claims, No Drawings

PROCESS FOR PRODUCING OPTICALLY ACTIVE AZETIDINE-2-CARBOXYLIC ACIDS

TECHNICAL FIELD

The present invention relates to a process for producing optically active azetidine-2-carboxylic acids, which is useful as an intermediate for pharmaceutical compounds.

BACKGROUND ART

In the art, the following methods are known for the production method of optically active azetidine-2-carboxylic acid derivatives.

(1) The method which comprises reacting L-2,4-diaminobutyric acid with hydrochloric acid-nitric acid to prepare a L-4-amino-2-chlorobutyric acid and subjecting the same to heat treatment in an aqueous solution of barium hydroxide to give D-azetidine-2-carboxylic acid [Biochemical Journal, vol. 64, page 323 (1956)].

(2) The method which comprises reacting γ-butyrolactone with bromine in the presence of red phosphorus, treating the reaction product with hydrogen chloride gas-saturated benzyl alcohol to prepare benzyl DL-2,4-dibromobutyrate, reacting the obtained product with benzhydrylamine to prepare benzyl DL-N-diphenylmethylazetidine-2-carboxylate, reducing the reaction product with hydrogen in methanol in the presence of palladium carbon to prepare DL-azetidine-2-carboxylic acid, reacting the obtained product with benzyloxycarbonyl chloride to prepare DL-N-(benzyloxycarbonyl)azetidine-2-carboxylic acid, subjecting the reaction product to optical resolution using L-tyrosine hydrazide to prepare L-N-(benzyloxycarbonyl)-azetidine-2-carboxylic acid and finally reducing the same again with hydrogen in methanol in the presence of palladium carbon to give L-azetidine-2-carboxylic acid [Journal of Heterocyclic Chemistry, vol. 6, pages 435 and 993 (1969)].

(3) The method which comprises S-alkylating L-N-(tosyl) methionine to prepare L-N-(tosyl)methionine sulfonium salt, converting the same to L-N-tosyl-α-amino-γ-butyrolactone by heating in an aqueous solution of sodium hydroxide, treating the lactone with a hydrogen halide gas in an alcohol to prepare alkyl L-N-tosyl-2-amino-4-halobutyrate, subjecting the reaction product to ring closure reaction in dimethylformamide with sodium hydride to prepare L-N-(tosyl)azetidine-2-carboxylic acid, and allowing the tosyl group to be eliminated from the reaction product in liquid ammonia using metallic sodium to give L-azetidine-2-carboxylic acid [Chemistry Letters, page 5 (1973)].

(4) The method which comprises cyclizing an L-aspartic acid diester to prepare 4-oxo-2-azetidinecarboxylic acid derivative, reducing the same with lithium aluminum hydride to prepare L-azetidine-2-methanol, N-tert-butoxycarbonylating the reaction product to prepare N-(tert-butoxycarbonyl)azetidine-2-methanol and oxidizing the reaction product to prepare L-N-(tert-butoxycarbonyl)azetidine-2-carboxylic acid, followed by deprotection to give L-azetidine-2-carboxylic acid (WO 9847867).

These methods, however, have problems such as mentioned below.

As for the method (1), L-2,4-diaminobutyric acid is expensive and, for obtaining the more useful L-form of azetidine-2-carboxylic acid, the more expensive D-form of 2,4-diaminobutyric acid is required. In addition, it is necessary to carry out the reaction procedure in the first step more strictly since the reaction temperature, reaction time and other conditions in that step influence the optical purity of the desired compound.

As for the method (2), the process is lengthy and, in addition, benzhydrylamine is expensive. Furthermore, the unrequired optically active substance obtained by optical resolution will be discarded unless an advantageous method of racemization thereof is found and it is economically disadvantageous.

As for the method (3), the process is lengthy and, in addition, the use of metallic sodium in liquid ammonia in the step of tosyl group elimination requires the use of a low-temperature apparatus and needs the caution in handling the same.

As for the method (4), lithium aluminum hydride, which needs caution in handling, is used as a reducing agent of azetidinone and this produces problems in industrialization.

Thus, as an industrial production method, each of the conventional production methods has problems to be solved.

Meanwhile, as methods for preparing optically active N-(alkoxycarbonyl)azetidine-2-carboxylic acids, the method comprising converting a mixture of optical isomers of azetidine-2-carboxylic acid to N-(benzyloxycarbonyl) azetidine-2-carboxylic acid by reacting with benzyloxycarbonyl chloride and optically resolving the resulting product using optically active tyrosine hydrazide (Journal of Heterocyclic Chemistry, page 993 (1969)) and the method comprising optically resolving a mixture of optical isomers of azetidine-2-carboxylic acid using optically active tartaric acid to prepare optically active azetidine-2-carboxylic acid (WO 9702241), followed by tert-butyloxycarbonylating the optical isomer obtained (Heterocylces, page 2539 (1986)) are known in the art.

However, in all of the above methods, it is necessary to use an expensive optically active resolving agent and, in addition, there is a problem that a number of multi-stage steps is required, such as the step of resolving agent separation.

In view of the above-mentioned state of the art, it is an object of the present invention to provide a production method of an optically active azetidine-2-carboxylic acid which method is efficient and economical and can be carried out in an industrially advantageous manner.

Further, in view of the above-mentioned state of the art, it is another object of the invention to provide a method for preparing an optically active N-(alkoxycarbonyl)azetidine-2-carboxylic acid with high optical purity in one stage step from a mixture of optical isomers of the N-(alkoxycarbonyl) azetidine-2-carboxylic acid, without using any expensive optical resolution agent.

DISCLOSURE OF INVENTION

The first aspect of the present invention provides a production method of an optically active N-protected azetidine-2-carboxylic acid represented by the general formula (5):

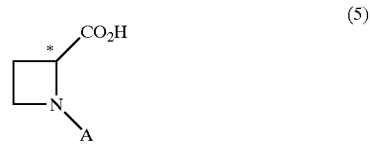

in the formula, A represents an amino group-protecting group and * represents an asymmetric carbon atom, which comprises halogenating an optically active 3-hydroxy-2-pyrrolidinone represented by the general formula (1):

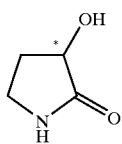
(1)

in the formula, * represents an asymmetric carbon atom, with inversion of configuration to prepare an optically active 3-halo-2-pyrrolidinone represented by the general formula (2):

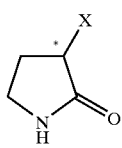
(2)

in the formula, X represents a halogen atom and * represents an asymmetric carbon atom, hydrolyzing the same to prepare an optically active 4-amino-2-halobutyric acid represented by the general formula (3):

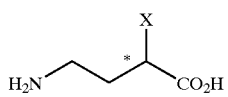
(3)

in the formula, X represents a halogen atom and represents an asymmetric carbon atom, cyclizing the reaction product in an alkaline aqueous solution to prepare an optically active azetidine-2-carboxylic acid represented by the general formula (4):

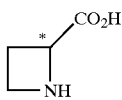
(4)

in the formula, * represents an asymmetric carbon atom, followed by treating the reaction product with an amino group-protecting agent.

The first aspect of the present invention also consists in:

a production method of an optically active 3-halo-2-pyrrolidinone (2)

which comprises halogenating an optically active 3-hydroxy-2-pyrrolidinone (1) with inversion of configuration;

a production method of an optically active 4-amino-2-halobutyric acid (3)

which comprises hydrolyzing an optically active 3-halo-2-pyrrolidinone (2);

a production method of an optically active 4-amino-2-halobutyric acid (3) which comprises halogenating an optically active 3-hydroxy-2-pyrrolidinone (1) with inversion of configuration to prepare an optically active 3-halo-2-pyrrolidinone (2)

followed by hydrolysis; and a production method of an optically active azetidine-2-carboxylic acid (4)

which comprises halogenating an optically active 3-hydroxy-2-pyrrolidinone (1) with inversion of configuration to prepare an optically active 3-halo-2-pyrrolidinone (2), hydrolyzing the same to prepare an optically active 4-amino-2-halobutyric acid (3), followed by cyclizing the reaction product in an alkaline aqueous solution.

The second aspect of the present invention provides a production method of an optically active N-protected azetidine-2-carboxylic acid represented by the above general formula (5)

which comprises halogenating an optically active 4-amino-2-hydroxybutyric acid ester represented by the general formula (6):

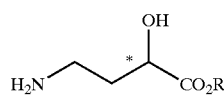
(6)

in the formula, R represents an ester-type protective group and * represents an asymmetric carbon atom, with inversion of configuration to prepare an optically active 4-amino-2-halobutyric acid ester represented by the general formula (7):

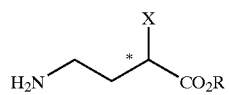
(7)

in the formula, R represents an ester-type protective group, X represents a halogen atom and * represents an asymmetric carbon atom, hydrolyzing the same to prepare an optically active 4-amino-2-halobutyric acid represented by the above general formula (3), cyclizing the reaction product in an alkaline aqueous solution to prepare an optically active azetidine-2-carboxylic acid represented by the above general formula (4), followed by treating the reaction product with an amino group-protecting agent.

The second aspect of the present invention also consists in:

a production method of an optically active 4-amino-2-halobutyric acid ester (7)

which comprises halogenating an optically active 4-amino-2-hydroxybutyric acid ester (6) with inversion of configuration;

a production method of an optically active 4-amino-2-halobutyric acid (3)

which comprises hydrolyzing an optically active 4-amino-2-halobutyric acid ester (7);

a production method of an optically active 4-amino-2-halobutyric acid (3)

which comprises halogenating an optically active 4-amino-2-hydroxybutyric acid ester (6) with inversion of configuration to prepare an optically active 4-amino-2-halobutyric acid ester (7)

followed by hydrolysis; and a production method of an optically active azetidine-2-carboxylic acid (4)

which comprises halogenating an optically active 4-amino-2-hydroxybutyric acid ester (6) with inversion of configuration to prepare an optically active 4-amino-2-halobutyric acid ester (7), hydrolyzing the same to prepare an optically active 4-amino-2-halobutyric acid (3) followed by cyclizing the reaction product in an alkaline aqueous solution.

The third aspect of the present invention provides a production method of an optically active N-protected azetidine-2-carboxylic acid represented by the above general formula (5)

which comprises halogenating an optically active 4-amino-2-hydroxybutyric acid ester represented by the general formula (6) with inversion of configuration to prepare an optically active 4-amino-2-halobutyric acid ester represented by the above general formula (7), cyclizing the same to prepare an optically active 3-halo-2-pyrrolidinone represented by the above general formula (2), hydrolyzing the reaction product to prepare an optically active 4-amino-2-halobutyric acid represented by the above general formula (3), cyclizing the reaction product in an alkaline aqueous solution to prepare an optically active azetidine-2-carboxylic acid represented by the above general formula (4), followed by treating the reaction product with an amino group-protecting agent.

The third aspect of the present invention also consists in:

a production method of an optically active 3-halo-2-pyrrolidinone (2)

which comprises cyclizing an optically active 4-amino-2-halobutyric acid ester (7);

a production method of an optically active 3-halo-2-pyrrolidinone (2)

which comprises halogenating an optically active 4-amino-2-hydroxybutyric acid ester (6) with inversion of configuration to prepare an optically active 4-amino-2-halobutyric acid ester (7)

followed by cyclization;

a production method of an optically active 4-amino-2-halobutyric acid (3)

which comprises halogenating an optically active 4-amino-2-hydroxybutyric acid ester (6) with inversion of configuration to prepare an optically active 4-amino-2-halobutyric acid ester (7), cyclizing the same to prepare an optically active 3-halo-2-pyrrolidinone (2)

followed by hydrolysis; and a production method of an optically active azetidine-2-carboxylic acid (4)

which comprises halogenating an optically active 4-amino-2-hydroxybutyric acid ester (6) with inversion of configuration to prepare an optically active 4-amino-2-halobutyric acid ester (7), cyclizing the same to prepare an optically active 3-halo-2-pyrrolidinone (2), hydrolyzing the reaction product to prepare an optically active 4-amino-2-halobutyric acid (3)

followed by cyclizing the reaction product in an alkaline aqueous solution.

The fourth aspect of the present invention provides a method for obtaining an optically active N-(alkoxycarbonyl)azetidine-2-carboxylic acid which comprises dissolving a mixture of optical isomers of an N-(alkoxycarbonyl)azetidine-2-carboxylic acid represented by the general formula (5'):

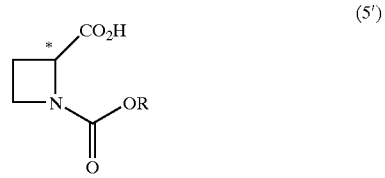

(5')

in the formula, R represents an alkyl group, which may optionally be substituted, and * represents an asymmetric carbon atom, in a solvent followed by a crystallization to thereby increase the optical purity of the N-(alkoxycarbonyl) azetidine-2-carboxylic acid represented by the general formula (5').

The reaction routes involved in the present invention may be illustrated as follows:

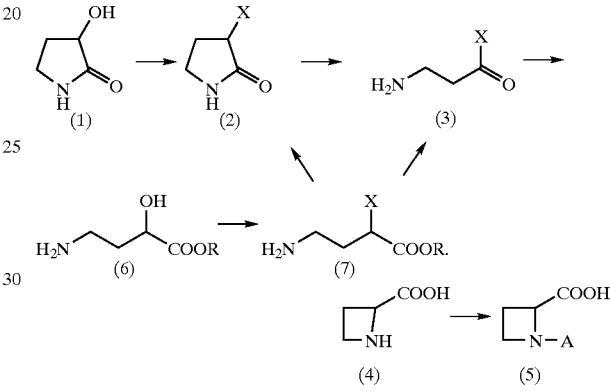

In the following, the present invention is described in detail.

Here, the first to third aspects of the present invention are explained taking the production methods of an optically active N-protected azetidine-2-carboxylic acid (5) as examples. The other production methods can be carried out in the same manner as mentioned hereinafter.

First, the first aspect of the invention is described.

In the production method of an optically active N-protected azetidine-2-carboxylic acid (5) according to the first aspect of the invention, first of all, an optically active 3-halo-2-pyrrolidinone represented by the general formula (2) is produced by halogenating an optically active 3-hydroxy-2-pyrrolidinone represented by the general formula (1) with inversion of configuration.

The thus-obtained optically active 3-halo-2-pyrrolidinone (2) is a novel compound and in which X is particularly preferably a chlorine atom.

The optically active 3-hydroxy-2-pyrrolidinone (1) to be used in accordance with the present invention can be synthesized, for example, by derived from malic acid [Tetrahedron, vol. 53, page 9213 (1997)].

In the general formula (2) or in the general formula (3) to be referred to later herein, X represents a halogen atom, for example a chlorine, bromine, iodine or fluorine. From the viewpoint of reactivity in subsequent steps and of racemization prevention, a chlorine or a bromine is particularly preferred.

A halogenating agent to be used for halogenating optically active 3-hydroxy-2-pyrrolidinone (1) is not particularly restricted but includes, for example, fluorinating agents such as hydrofluoric acid-potassium fluoride; chlorinating agents such as thionyl chloride, phosphorus trichloride, phosphorus pentachloride, hydrochloric acid, phosphorus oxychloride and triphenylphosphine-carbon tetrachloride; brominating agents such as thionyl bromide, thionyl chloride-hydrobromic acid, phosphorus tribromide, hydrobromic acid, and triphenylphosphine-carbon tetrabromide; and iodinating agents such as hydroiodic acid, triphenylphosphine-iodine and trimethylchlorosilane-sodium iodide. From the viewpoint of ease in handling and of stereoselectivity, thionyl chloride, thionyl bromide and thionyl chloride-hydrobromic acid are preferred, and thionyl chloride is particularly preferred.

The amount of the halogenating agent to be used is not particularly restricted. Generally, the halogenation can be carried out using the agent in an amount of not less than 1 mole equivalent relative to 3-hydroxy-2-pyrrolidinone (1). From the economic viewpoint, generally preferred is the use of not more than 10.0 mole equivalents, more preferably not more than 5.0 mole equivalents, still more preferably not more than 2.0 mole equivalents.

The reaction solvent in carrying out the halogenation is not particularly restricted but includes, for example, hydrocarbon solvents such as pentane, hexane, heptane, cyclohexane and petroleum ether; ester solvents such as ethyl acetate, methyl acetate, propyl acetate and methyl propionate; aromatic hydrocarbon solvents such as toluene, benzene and xylene; nitrile solvents such as acetonitrile and propionitrile; ether solvents such as tert-butyl methyl ether, diethyl ether, diisopropyl ether, tetrahydrofuran and dioxane; ketone solvents such as acetone and ethyl methyl ketone; amide solvents such as N,N-dimethylformamide and N,N-dimethylacetamide; sulfoxide solvents such as dimethyl sulfoxide; halogenated hydrocarbon solvents such as methylene chloride, chloroform and carbon tetrachloride; and thionyl chloride. Two or more of these solvents may also be used in admixture. From the viewpoint of solubility of 3-hydroxy-2-pyrrolidinone (1) and of stability against halogenating agents, dioxane, tetrahydrofuran, ethylene glycol dimethyl ether and thionyl chloride and mixed solvents of two or more of these are preferred. When a mixed solvent is used, the mixing ratio is not particularly restricted.

While the concentration of 3-hydroxy-2-pyrrolidinone (1) in carrying out the halogenation reaction may vary depending on the reaction solvent, the reaction can be carried out generally at the concentration of 1 to 50% by weight, preferably 5 to 30% by weight.

The reaction temperature for the halogenation reaction may vary depending on the species of the halogenating agent and reaction solvent employed. Generally, it is in the range of from the freezing point to the boiling point of the reaction solvent employed. For driving the reaction to be completed in a short time, it is recommended that the temperature be elevated. From the viewpoint of stereoselectivity of reaction, it is recommended to select a low temperature. Generally, the temperature is 20 to 100° C., preferably 30 to 60° C.

The reaction time for the halogenation reaction may vary depending on the species of the halogenating agent and reaction solvent employed and on the reaction temperature. When the reaction is carried out at a temperature of 30 to 60° C., for instance, the reaction time is generally about 1 to 24 hours.

The halogenation reaction may proceed without particular addition of a catalyst. When a catalyst is to be added, however, a tertiary amine and N,N-dimethylformamide are preferred from the viewpoint of improvement in rate of reaction and of stereoselectivity. Among them, pyridine, triethylamine, imidazole or N,N-dimethylformamide is preferably used.

The amount of the catalyst to be used is not particularly restricted but the reaction can be carried out using a catalyst in an amount of not less than 0.01 mole percent but not more than 100 mole percent relative to 3-hydroxy-2-pyrrolidinone (1) From the economic viewpoint, it is generally preferable to use it in an amount of not less than 0.1 mole percent but not more than 20 mole percent, more preferably not less than 0.5 mole percent but not more than 10 mole percent.

When a volatile halogenating agent, for example thionyl chloride, is used, 3-halo-2-pyrrolidinone (2) can be obtained as a raw product, after carrying out the halogenation reaction in the above manner, by merely distilling off the reaction solvent under reduced pressure, and the raw product can be used as it is in the next step. When a nonvolatile halogenating agent is used, 3-halo-2-pyrrolidinone (2) can be obtained with relatively high purity by quenching the halogenating agent with water, neutralizing the aqueous layer and extracting the product into the organic layer. In cases where a tertiary amine is used as the catalyst, the organic layer is preferably washed with weakly acidic water.

In the second step, an optically active 4-amino-2-halobutyric acid represented by the general formula (3) or a salt thereof is produced by hydrolyzing the optically active 3-halo-2-pyrrolidinone represented by the general formula (2).

As the solvent in the hydrolysis reaction, there may be mentioned water alone, or a mixed solvent composed of water and a water-soluble organic solvent. The water-soluble organic solvent includes, for example, tetrahydrofuran, dioxane, methanol, ethanol or the like.

From the viewpoint of increasing the rate of reaction, an acid or a base is preferably used for the hydrolysis reaction. The acid to be used includes, for example, inorganic acids such as sulfuric acid, hydrochloric acid, phosphoric acid, nitric acid, carbonic acid and perchloric acid; and organic acids such as p-toluenesulfonic acid, methanesulfonic acid, trifluoromethanesulfonic acid, acetic acid, formic acid, trifluoroacetic acid and the like. From the viewpoint of side reaction prevention, acids lower in nucleophilicity, for example sulfuric acid, perchloric acid, p-toluenesulfonic acid and methanesulfonic acid are more preferred. The base to be used includes, for example, alkali metal bases such as sodium hydroxide, cesium hydroxide, potassium hydroxide, lithium hydroxide and cesium carbonate; and alkaline earth metal bases such as barium hydroxide and calcium hydroxide. Among them, sodium hydroxide and barium hydroxide are preferred. From the viewpoint of racemization prevention, the use of an acid is preferred to the use of a base and, further, the use of an acid lower in nucleophilicity, for example sulfuric acid, methanesulfonic acid or p-toluenesulfonic acid, is more preferred. In accordance with a preferred embodiment of the invention, the hydrolysis reaction is carried out in an acidic aqueous solution, more preferably in a sulfuric acid aqueous solution.

The amount of the acid or base to be used is not particularly restricted. Generally, however, the reaction can be carried out using the acid or base in an amount not less than 1 mole equivalent but not more than 100 mole equivalents relative to 3-halo-2-pyrrolidinone (2). For economic reasons, the use of not less than 1 mole equivalent to not more than 20 mole equivalents is generally preferred.

The concentration of 3-halo-2-pyrrolidinone (2) in carrying out the hydrolysis reaction is generally 1 to 50% by weight, preferably 2 to 30% by weight.

The reaction temperature for the hydrolysis reaction may vary depending on the species of the acid or base employed but generally is in the range of from the freezing point to the boiling point of water, which is the reaction solvent. For driving the reaction to be completed in a short time, it is recommended that the temperature be elevated while, from the viewpoint of racemization prevention, it is recommended that a low temperature be selected. Thus, the temperature is generally 20 to 100° C., preferably 50 to 100° C.

The reaction time for the hydrolysis reaction may vary depending on the species of the acid or base employed, on the number of equivalents thereof and on the reaction temperature. When the reaction is carried out at a temperature of 80 to 90° C., the reaction time is generally about 1 to 24 hours.

After completion of the hydrolysis reaction in the above manner, the reaction solution, when occurring as an acidic aqueous solution, is neutralized with a base, after which it can be submitted to the cyclization reaction in the next step. When it occurs as an alkaline aqueous solution, it can be submitted as such to the next step. In either case, the hydrolysis product can be isolated, if necessary. When the acid or base, to be used is volatile, for example in the case of hydrochloric acid, the salt of optically active 4-amino-2-halobutyric acid (3) can be isolated by merely distilling off the reaction solvent under reduced pressure. When the acid or base used is nonvolatile, optically active 4-amino-2-halobutyric acid (3) can be isolated by purifying the reaction solution by ion exchange chromatography or the like.

In the third step, an optically active azetidine-2-carboxylic acid represented by the general formula (4) is produced by cyclizing the optically active 4-amino-2-halobutyric acid represented by the general formula (3) in an alkaline aqueous solution.

The base to be used in the alkaline aqueous solution includes, for example, alkali metal bases such as sodium hydroxide, cesium hydroxide, potassium hydroxide, lithium hydroxide and cesium carbonate; and alkaline earth metal bases such as barium hydroxide and calcium hydroxide. Among them, sodium hydroxide and barium hydroxide are preferred.

The amount of the base to be used is not particularly restricted but, generally, the reaction can be carried out using the base in an amount of not less than 1 mole equivalent but not more than 30 mole equivalents relative to 4-amino-2-halobutyric acid (3). Generally, the use of not less than 1 mole equivalent to not more than 10 mole equivalents is preferred.

The concentration of 4-amino-2-halobutyric acid (3) in carrying out the cyclization reaction is generally 1 to 50% by weight, preferably 2 to 30% by weight.

The reaction temperature for the cyclization reaction may vary depending on the species of the base employed but generally is in the range of from the freezing point to the boiling point of water, which is the reaction solvent. For driving the reaction to be completed in a short time, it is recommended that the temperature be elevated while, from the viewpoint of racemization prevention, it is recommended that a low temperature be selected. Thus, the temperature is generally 30 to 100° C., preferably 50 to 100° C.

The reaction time for the cyclization reaction may vary depending on the species of the base employed, on the number of equivalents thereof and on the reaction temperature. When the reaction is carried out at a temperature of 80 to 100° C., the reaction time is generally about 20 minutes to about 12 hours.

After completion of the cyclization reaction in the above manner, the reaction solution is merely neutralized with an acid, after which it can be submitted to the amino group-protecting reaction in the next step. If necessary, optically active azetidine-2-carboxylic acid (4) can be isolated by purifying the reaction solution by ion exchange chromatography or the like.

In the fourth step, an optically active N-protected azetidine-2-carboxylic acid represented by the general formula (5) is produced by treating the optically active azetidine-2-carboxylic acid represented by the general formula (4) with an amino group-protecting agent.

Referring to the general formula (5), A represents an amino group-protecting group. The amino group-protecting group is not particularly restricted but includes, for example, alkoxycarbonyl type protective groups such as tert-butoxycarbonyl, benzyloxycarbonyl, allyloxycarbonyl, methoxycarbonyl and ethoxycarbonyl groups; acyl type protective groups such as benzoyl, acetyl and trifluoroacetyl groups; sulfonyl type protective groups such as p-toluenesulfonyl and methanesulfony groups; and alkyl type protective groups such as allyl, benzyl and benzhydryl groups. Generally, alkoxycarbonyl groups are preferred. In view of their easiness of elimination and easiness of extract from aqueous solutions with organic solvents, tert-butoxycarbonyl, benzyloxycarbonyl, benzoyl, benzyl and like groups are preferred, and a tert-butoxycarbonyl group is particularly preferred.

The amino group-protecting agent to be used in the above amino group-protecting reaction is not particularly restricted but includes, for example, alkoxycarbonyl type protecting agents such as di-tert-butyl dicarbonate, benzyl chlorocarbonate, methyl chlorocarbonate, ethyl chlorocarbonate and allyl chlorocarbonate; acyl type protecting agents such as benzoyl chloride, acetyl chloride, trifluoroacetyl chloride and acetic anhydride; sulfonyl type protecting agents such as p-toluenesulfonyl chloride and methanesulfonyl chloride; and alkyl type protecting agents such as allyl chloride and benzyl chloride. Among them, di-tert-butyl dicarbonate, benzyl chlorocarbonate, benzoyl chloride and the like are preferred in view of easiness of elimination and of easiness of extract from aqueous solutions with organic solvents.

The amount of the amino group-protecting agent to be used is preferably in an amount of 1 to 3 mole equivalents, more preferably 1 to 1.5 mole equivalents relative to azetidine-2-carboxylic acid (4).

When a chlorocarbonate ester type protecting agent, an acetyl chloride type protecting agent or di-tert-butyl dicarbonate is used as the amino group-protecting agent, water, toluene, ethyl acetate, tetrahydrofuran and like solvents used each alone or mixed solvents of these, for instance, are used as the reaction solvent. In cases where the amino group-protecting agent is a sulfonyl chloride type protecting agent, organic solvents such as toluene, ethyl acetate, tetrahydrofuran and the like used each alone or mixed solvents of these are used.

The above amino group-protecting reaction is carried out in the presence of a base. The base to be used is not particularly restricted but includes, for example, inorganic bases such as sodium carbonate, sodium hydrogen carbonate, sodium hydroxide and potassium hydroxide; and organic bases such as triethylamine, pyridine and N-methylmorpholine. The amount of the base to be used is 1 to 10 mole equivalents, preferably 1 to 3 mole equivalents, relative to the amino group-protecting agent.

The reaction temperature for the amino group-protecting reaction is not particularly restricted but is in the range of not lower than the freezing point to not higher than the boiling point of the solvent employed. It is generally 0 to 100° C., preferably 20 to 70° C. The reaction time is preferably 1 to 20 hours, more preferably 2 to 10 hours.

After completion of the above amino group-protecting reaction, the reaction is stopped by adding dilute hydrochloric acid, an aqueous solution of ammonium chloride or the like and the reaction solution is then made weakly acidic. Then, the product is extracted with a solvent such as ethyl acetate, diethyl ether or toluene, and the extract is washed with a saturated aqueous solution of sodium hydrogen carbonate, a saturated aqueous solution of sodium chloride or the like, then dried over a drying agent such as sodium sulfate or magnesium sulfate, filtered and concentrated, followed by a routine procedure such as recrystallization and/or column chromatography, whereby N-protected azetidine-2-carboxylic acid (5) can be isolated.

In case N-protected azetidine-2-carboxylic acid obtained is low in optical purity, the optical purity can be improved by recrystallization. The technique for this recrystallization is the same as described later herein referring to the fourth aspect of the present invention.

The second aspect of the invention is now described.

In accordance with the invention, an optically active 4-amino-2-halobutyric acid ester represented by the general formula (7) is first produced by halogenating an optically active 4-amino-2-hydroxybutyric acid ester represented by the general formula (6) with inversion of configuration.

The optically active 4-amino-2-halobutyric acid ester represented by the general formula (7) is a novel compound and, in this compound, X represents a halogen atom, for example a chlorine, bromine, iodine or fluorine. From the viewpoint of reactivity and of racemization prevention in the subsequent steps, a chlorine and a bromine are particularly preferred and, among them, a chlorine is preferred.

In the above compound, R represents an ester type protective group, for example an alkyl group containing 1 to 10 carbon atoms, an aryl group containing 6 to 20 carbon atoms, an aralkyl group containing 7 to 20 carbon atoms or a silyl group-protective group. These groups may be straight-chained or branched. Such groups are not particularly restricted but include, for example, methyl, ethyl, n-propyl, isopropyl, n-butyl, isobutyl, tert-butyl, phenyl, benzyl, α-methylbenzyl phenylpropyl and like groups. Preferred among these are alkyl groups containing 1 to 10 carbon atoms and aralkyl groups containing 7 to 10 carbon atoms, such as methyl, ethyl, n-propyl, isopropyl, tert-butyl and benzyl groups. More preferred are alkyl groups containing 1 to 4 carbon atoms. Methyl group is particularly preferred. The above R may partly be substituted by a substituent. The substituents are not particularly restricted but include, for example, halogen, nitro, hydroxyl, ether, amide and like groups.

From the viewpoint of easy availability or of stability, the optically active 4-amino-2-halobutyric acid ester represented by the general formula (7) may be in the form of an acid-derived salt. As such acid-derived salt, there may be mentioned, for example, inorganic acid salts such as hydrochloride, sulfate, hydrobromide, hydrofluoride, phosphate, nitrate and perchlorate, sulfonic acid salts such as p-toluenesulfonate and methanesulfonate, and carboxylic acid salts such as trifluoroacetate, acetate and benzoate, of the optically active 4-amino-2-halobutyric acid ester. Among them, the hydrochloride, sulfate, p-toluenesulfonate and methanesulfonate salts are preferred in view of their easy availability and low counter anion nucleophilicity. In particular, the hydrochloride salt is preferred.

The optically active 4-amino-2-hydroxybutyric acid ester (6) to be used in accordance with the present invention can be synthesized, for example, by converting L-glutamic acid into the corresponding cyclic lactone with nitrous acid, converting the lactone to a monoamide by ring opening with ammonia and subjecting it to Hofmann degradation with antiformin to give L-4-amino-2-hydroxybutyric acid (Japanese Kokai Publication Sho-50-4019), finally followed by esterification according to the conventional method. When the esterification is carried out under thionyl chloride-alcohol condition, optically active 4-amino-2-hydroxybutyrate hydrochloride can be obtained by merely concentrating the reaction solution after completion of the reaction.

From the viewpoint of easy availability, optically active 4-amino-2-hydroxybutyric acid ester to be used in the present invention represented by the general formula (6) may be in the form of an acid-derived salt in view of their easy availability. As such acid-derived salt, there may be mentioned, for example, inorganic acid salts such as hydrochloride, sulfate, hydrobromide, hydrofluoride, phosphate, nitrate and perchlorate, sulfonic acid salts such as p-toluenesulfonate and methanesulfonate, and carboxylic acid salts such as trifluoroacetate, acetate and benzoate, of the optically active-4-amino-2-hydroxybutyric acid ester. Among them, the hydrochloride, sulfate, p-toluenesulfonate and methanesulfonate are preferred in view of their easy availability.

The halogenating agent to be used for halogenating 4-amino-2-hydroxybutyric acid ester (6) includes, for example, fluorinating agents such as hydrofluoric acid-potassium fluoride; chlorinating agents such as thionyl chloride, phosphorus trichloride, phosphorus pentachloride, hydrochloric acid, phosphorus oxychloride and triphenylphosphine-carbon tetrachloride; brominating agents such as thionyl bromide, thionyl chloride-hydrobromic acid, phosphorus tribromide, hydrobromic acid, and triphenylphosphine-carbon tetrabromide; and iodinating agents such as hydroiodic acid, triphenylphosphine-iodine and trimethylchlorosilane-sodium iodide. From the viewpoint of ease in handling and of stereoselectivity, thionyl chloride, thionyl bromide and thionyl chloride-hydrobromic acid are preferred, and thionyl chloride is particularly preferred.

The amount of the halogenating agent to be used is not particularly restricted. Generally, the halogenation can be carried out using the agent in an amount of not less than 1 mole equivalent relative to 4-amino-2-hydroxybutyric acid ester (6) From the economic viewpoint, the use of not more than 10.0 mole equivalents is generally preferred, more preferably not more than 5.0 mole equivalents, still more preferably not more than 2.0 mole equivalents.

The reaction solvent in carrying out the halogenation is not particularly restricted unless the reaction is adversely affected. Thus, it includes, for example, hydrocarbon solvents such as pentane, hexane, heptane, cyclohexane and petroleum ether; ester solvents such as ethyl acetate, methyl acetate, propyl acetate and methyl propionate; aromatic hydrocarbon solvents such as toluene, benzene and xylene; nitrile solvents such as acetonitrile and propionitrile; ether solvents such as tert-butyl methyl ether, diethyl ether, diisopropyl ether, tetrahydrofuran and dioxane; ketone solvents such as acetone and ethyl methyl ketone; amide solvents such as N,N-dimethylformamide and N,N-dimethylacetamide; sulfoxide solvents such as dimethyl sulfoxide; halogenated hydrocarbon solvents such as methylene chloride, chloroform and carbon tetrachloride; and thionyl chloride. Two or more of these solvents may also be used in admixture. From the viewpoint of solubility of 4-amino-2-hydroxybutyric acid ester (6) and of stability against halogenating agents, dioxane, tetrahydrofuran, ethylene glycol dimethyl ether and thionyl chloride and mixed solvents of two or more of these are preferred. When a mixed solvent is used, the mixing ratio is not particularly restricted.

While the concentration of 4-amino-2-hydroxybutyric acid ester (6) in carrying out the halogenation reaction may vary depending on the reaction solvent employed, the reaction can be carried out generally in the concentration of 1 to 50% by weight, preferably 5 to 30% by weight.

The reaction temperature for the halogenation reaction may vary according to the halogenating agent and reaction solvent employed. Generally, it is in the range from the freezing point to the boiling point of the reaction solvent employed. For driving the reaction to be completed in a short time, it is recommended that the temperature be elevated while, from the viewpoint of stereoselectivity, it is recommended that a low temperature be selected. Thus, the temperature is generally 20 to 100° C., preferably 30 to 60° C.

The reaction time for the halogenation reaction may vary depending on the species of the halogenating agent and reaction solvent employed and on the reaction temperature. When the reaction is carried out at a temperature of 30 to 60° C., the reaction time is generally about 1 to 24 hours.

The halogenation reaction may proceed without particular addition of a catalyst. From the viewpoint of improvement of reaction rate and of stereoselectivity, however, the addition of a tertiary amine or N,N-dimethylformamide is preferred, and pyridine, triethylamine, imidazole or N,N-dimethylformamide is preferably used among them.

The amount of the catalyst to be used is not particularly restricted but, generally, the reaction can be carried out using a catalyst in an amount of not less than 0.01 mole percent but not more than 100 mole percent relative to 4-amino-2-hydroxybutyric acid ester (6). From the economic viewpoint, it is generally preferred to use it in an amount of not less than 0.1 mole percent but not more than 20 mole percent, more preferably within the range of not less than 0.5 mole percent to not more than 10 mole percent.

In cases where a thionyl halide type halogenating agent, such as thionyl chloride, is used in the halogenation reaction, 4-amino-2-hydroxybutyric acid ester (6) may aggregate into a mass in the reaction system in some instances. Although the reaction can proceed without any trouble even in such cases, this aggregation can be avoided when hydrogen chloride is caused to coexist in the reaction solution. The amount of hydrogen chloride to be used is not particularly restricted if it is not more than the amount of saturation solubility level relative to the reaction solvent. A preferred amount, however, is not less than 1.0 mole equivalent but not more than 20 mole equivalents relative to 4-amino-2-hydroxybutyric acid ester (6).

When a volatile halogenating agent, such as thionyl chloride, is used after carrying out the halogenation reaction in the above manner, 4-amino-2-halobutyric acid ester (7) can be obtained in the form of hydrochloride by merely distilling off the reaction solvent under reduced pressure, and the product can be used as it is in the next step. When a nonvolatile halogenating agent is used, the halogenating agent is quenched with water or the like, and the resulting product can be used as it is in the next step.

In the subsequent second step, an optically active 4-amino-2-halobutyric acid represented by the general formula (3) is produced by hydrolyzing the optically active 4-amino-2-halobutyric acid ester represented by the general formula (7).

As the solvent in the hydrolysis reaction, there may be mentioned water alone, or a mixed solvent composed of water and a water-soluble organic solvent. The water-soluble organic solvent is, for example, tetrahydrofuran, dioxane, methanol, ethanol or the like.

From the viewpoint of increasing the rate of reaction, the hydrolysis reaction is preferably carried out using an acid or a base. The acid to be used includes, for example, inorganic acids such as sulfuric acid, hydrochloric acid, phosphoric acid, nitric acid, carbonic acid and perchloric acid, and organic acids such as p-toluenesulfonic acid, methanesulfonic acid, trifluoromethanesulfonic acid, acetic acid, formic acid, trifluoroacetic acid and the like. From the viewpoint of side reaction prevention, acids lower in nucleophilicity, for example sulfuric acid, perchloric acid, p-toluenesulfonic acid and methanesulfonic acid are more preferred. The base to be used includes, for example, alkali metal bases such as sodium hydroxide, cesium hydroxide, potassium hydroxide, lithium hydroxide and cesium carbonate, and alkaline earth metal bases such as barium hydroxide and calcium hydroxide. Among them, sodium hydroxide and barium hydroxide are preferred. From the viewpoint of racemization prevention, the use of an acid is preferred to the use of a base and, further, the use of an acid lower in nucleophilicity, for example sulfuric acid, methanesulfonic acid or p-toluenesulfonic acid, is more preferred. In accordance with a preferred embodiment of the invention, the hydrolysis reaction is carried out in an acidic aqueous solution, more preferably in a sulfuric acid aqueous solution.

The amount of the acid or base to be used is not particularly restricted. Generally, however, the reaction can be carried out using the acid or base in an amount not less than 1 mole equivalent but not more than 100 mole equivalents relative to 4-amino-2-halobutyric acid ester (7). From economic viewpoint, the use of not less than 1 mole equivalent to not more than 20 mole equivalents is generally preferred.

The concentration of 4-amino-2-halobutyric acid ester (7) in carrying out the hydrolysis reaction is generally 1 to 50% by weight, preferably 2 to 30% by weight.

The reaction temperature for the hydrolysis reaction may vary according to the species of the acid or base employed. Generally, it is in the range from the freezing point to the boiling point of the reaction solvent. For driving the reaction to be completed in a short time, it is recommended that the temperature be elevated while, from the viewpoint of racemization prevention, it is recommended that a low temperature be selected. Thus, the temperature is generally 20 to 100° C., preferably 20 to 50° C.

The reaction time for the hydrolysis reaction may vary depending on species and the number of equivalents of the acid or base employed and on the reaction temperature. When the reaction is carried out at a temperature of 20 to 50° C., the reaction time is generally about 1 to 24 hours.

After completion of the hydrolysis reaction in the above manner, the reaction solution, when occurring as an acidic aqueous solution, is neutralized with a base, after which it can be submitted to the cyclization reaction in the next step. When it occurs as an alkaline aqueous solution, it can be submitted as such to the next step. In either case, the hydrolysis product can be isolated, if necessary. When the acid or base used is volatile, for example in the case of hydrochloric acid, the salt of optically active 4-amino-2-halobutyric acid (3) can be isolated by merely distilling off the reaction solvent under reduced pressure. When the acid or base used is nonvolatile, optically active 4-amino-2-halobutyric acid (3) can be isolated by purifying the reaction solution by ion exchange chromatography or the like.

The subsequent third and fourth steps are the same as the third and fourth steps described hereinabove referring to the first aspect of the present invention.

The third aspect of the invention is now described.

The first step is the same as the first step described hereinabove referring to the second aspect of the present invention.

In the second step, an optically active 3-halo-2-pyrrolidinone (2) is produced by cyclizing the 4-amino-2-halobutyric acid ester (7).

The reaction solvent for the above cyclization reaction is not particularly restricted but includes, for example, hydrocarbon solvents such as pentane, hexane, heptane, cyclohexane and petroleum ether, ester solvents such as ethyl acetate, methyl acetate, propyl acetate and methyl propionate, aromatic hydrocarbon solvents such as toluene, benzene and xylene, nitrile solvents such as acetonitrile and propionitrile, ether solvents such as tert-butyl methyl ether, diethyl ether, diisopropyl ether, tetrahydrofuran and dioxane, ketone solvents such as acetone and ethyl methyl ketone, amide solvents such as N,N-dimethylformamide and N,N-dimethylacetamide, sulfoxide solvents such as dimethyl sulfoxide, halogenated hydrocarbon solvents such as methylene chloride, chloroform and carbon tetrachloride, and water. Two or more of these solvents may also be used in admixture. Among them, dioxane, tetrahydrofuran, ethyl acetate, chloroform, methylene chloride and water and mixed solvents of two or more of these are preferred. When a mixed solvent is used, the mixing ratio is not particularly restricted.

While the reaction temperature for the cyclization reaction may vary depending on the ester species of 4-amino-2-halobutyric acid ester (7), it is within the range of not lower than the freezing point to not higher than the boiling point of the solvent employed, thus generally at 0 to 100° C. From the viewpoint of racemization prevention, it is preferably within the range of 20 to 70° C. The reaction time in that case is preferably 3 minutes to 3 hours, more preferably 10 minutes to 1 hour.

The concentration of 4-amino-2-halobutyric acid ester (7) in carrying out the cyclization reaction can be generally of 1 to 50% by weight, preferably 2 to 30% by weight.

Generally, the cyclization reaction of 4-amino-2-halobutyric acid ester (7) proceeds spontaneously when the amino group is in a free form, although the rate more or less depends on the ester species. In the presence of abase, that reaction tends to be accelerated. In cases where 4-amino-2-halobutyric acid ester (7) is in the form of a salt with an acid, a base is required to liberate the amino group. The base to be used is not particularly restricted but includes, for example, inorganic bases such as sodium carbonate, sodium hydrogen carbonate, sodium hydroxide, potassium hydroxide and barium hydroxide, and organic bases such as triethylamine, pyridine and N-methylmorpholine. From the viewpoint of the stability of the product 3-halo-2-pyrrolidinone (2), sodium carbonate, sodium hydrogen carbonate, triethylamine and the like, which are low in nucleophilicity, are preferred. The amount of the base to be used is 1 to 10 mole equivalents relative to the salt composed of 4-amino-2-halobutyric acid ester (7) and an acid. From the viewpoint of the stability of the product 3-halo-2-pyrrolidinone (2), the amount is preferably as small as possible. More preferably, it is 1.0 to 1.5 mole equivalents.

When a water-soluble base insoluble in organic solvents, for example sodium carbonate, and the salt composed of 4-amino-2-halobutyric acid ester (7) and an acid are dissolved in water and a water-insoluble organic solvent is added to the solution to give a two-phase system, 3-halo-2-pyrrolidinone (2) formed as the progress of the reaction migrates into the organic layer. Thus, after the reaction, 3-halo-2-pyrrolidinone (2) can be obtained by separating the organic layer and distilling off the organic solvent.

When water is used as the reaction solvent, the thus-synthesized optically active 3-halo-2-pyrrolidinone (2) can be isolated by extracting with an organic solvent and distilling off the solvent, followed by such a conventional procedure as column chromatography or crystallization. In cases where an organic solvent is used, it is enough to distill off the solvent. When a base is used, however, the reaction solution is recommendably washed with an acidic aqueous solution.

The subsequent third, fourth and fifth steps are the same as the second, third and fourth steps, respectively, described hereinabove referring to the first aspect of the invention.

Finally, the fourth aspect of the present invention is now described.

In the present invention, R in the general formula (5') represents a hydrocarbon group, which may optionally be substituted. The group may be anyone capable of forming a —COOR generally known in the art as a easily eliminable amino group-protecting group, without any particular restriction. Preferred are tert-butyl, benzyl and allyl groups, and a tert-butyl group is more preferred.

The mixture of optical isomers of N-(alkoxycarbonyl) azetidine-2-carboxylic acid represented by the general formula (5') in the present invention is composed of a mixture of two optical isomers, namely the D and L forms. The mixing ratio between respective optical isomers is arbitrary but, preferably, either one of the optical isomers is higher in mixing proportion and, thus, for example, an optical purity of not less than 60% ee is preferred.

As for the mixture of the optical isomers of N-(alkoxycarbonyl)azetidine-2-carboxylic acid represented by the general formula (5') (hereinafter sometimes referred to as "optical isomer mixture" for short), which can appropriately be used in the practice of the invention, the one obtained by the production methods mentioned above or the one synthesized by converting 4-aminobutyric acid to bromide to prepare 4-amino-2-bromobutyric acid and cyclizing the same in an aqueous solution of barium hydroxide to give racemic azetidine-2-carboxylic acid [Biochemical Journal, page 323 (1956)], followed by N-alkoxycarbonylation according to the conventional method is preferably used.

The optical isomer mixture to be used in the practice of the invention is preferably a mixture of the optical isomers of N-(alkoxycarbonyl)azetidine-2-carboxylic acid represented by the general formula (5') in which mixing ratio of the optical isomers is biased to either one of the optical isomers. Such mixture can be obtained by the production methods mentioned hereinabove or can be synthesized by chlorinating optically active L-2,4-diaminobutyric acid, which is commercially available, with silver nitrite and hydrochloric acid to prepare the 4-amino-2-chlorobutyric acid and then cyclizing the same in an aqueous solution of barium hydroxide to give a mixture of the optical isomers of azetidine-2-carboxylic acid with a specific rotation of +102° (the specific rotation of the optically pure isomer being +123°) [Biochemical Journal, page 323 (1956)], followed by N-alkoxycarbonylation according to the conventional method.

In the practice of the invention, the solvent for dissolving the mixture of the optical isomers of N-(alkoxycarbonyl) azetidine-2-carboxylic acid represented by the general formula (5') is not particularly restricted but may be any of those capable of dissolving the optical isomer mixture to give a homogeneous solution. An organic solvent or a mixed solvent of two or more organic solvents is preferred, however. The organic solvent is not particularly restricted but includes, for example, hydrocarbon solvents such as pentane, hexane, heptane, cyclohexane and petroleum ether; ester solvents such as ethyl acetate, methyl acetate, propyl acetate and methyl propionate; aromatic hydrocarbon solvents such as toluene, benzene and xylene; nitrile solvents such as acetonitrile and propionitrile; ether solvents such as tert-butyl methyl ether, diethyl ether, diisopropyl ether, tetrahydrofuran and dioxane; alcohol solvents such as methanol, ethanol, isopropanol and n-propanol; ketone solvents such as acetone and ethyl methyl ketone; amide solvents such as N,N-dimethylformamide and N,N-dimethylacetamide; sulfoxide solvents such as dimethyl sulfoxide; halogenated hydrocarbon solvents such as methylene chloride, chloroform and carbon tetrachloride; etc. Two or more of these organic solvents may also be used in admixture. Among them, hydrocarbon solvents, aromatic hydrocarbon solvents, ester solvents, nitrile solvents and ether solvents are preferred, and hexane, ethyl acetate, toluene, acetonitrile and tert-butyl methyl ether as well as mixed solvents composed of two or more of these are particularly preferred. When a mixed solvent is used, the mixing ratio is not particularly restricted.

The amount of the solvent to be used may vary depending on the solvent employed or the heating temperature but is required to be at least such that the mixture of the optical isomers of N-(alkoxycarbonyl)azetidine-2-carboxylic acid represented by the general formula (5') can be dissolved at a temperature not higher than the boiling point of the solvent employed. From the viewpoint of crystallization yield, the amount of the solvent to be used is preferably as small as possible. Thus, it is more preferably within the range of 1 to 1.1 times the amount of the solvent which gives a saturated solution of the optical isomer mixture at a dissolution temperature. The solvent amount giving a saturated solution at the dissolution temperature can be determined in advance in the conventional manner.

The temperature at which the mixture of the optical isomers of N-(alkoxycarbonyl)azetidine-2-carboxylic acid represented by the general formula (5') is completely dissolved in a solvent is generally selected within the range of not lower than 0° C. to not higher than the boiling point of the solvent employed. From the crystallization yield viewpoint, it is preferably dissolved at not lower than 25° C., in particular not lower than 30° C.

After dissolution of the mixture of the optical isomers of N-(alkoxycarbonyl)azetidine-2-carboxylic acid represented by the general formula (5') in a solvent, the crystallization is preferably effected by cooling the solution, from the viewpoint of improving the crystallization yield. The temperature to which the solution is to be cooled (cooling temperature) can be appropriately selected. Generally, it is within the range of −80° C. to 25° C., preferably −40° C. to 25° C., more preferably −30° C. to 10° C. The rate of cooling is generally 1 to 50° C., preferably 3 to 25° C. per hour. The rate of cooling need not be constant but may be varied continuously or stepwise.

In cases where the isomer mixing ratio in the mixture of the optical isomers of N-(alkoxycarbonyl)azetidine-2-carboxylic acid represented by the general formula (5') is not biased to either one isomer, it is necessary, after dissolution of the optical isomer mixture in a solvent, to add seed crystals of one of both isomers to the solution and thereby cause that optical isomer to crystallize out preferentially. In cases where the isomer mixing ratio in the optical isomer mixture is biased to either one isomer, that optically active N-(alkoxycarbonyl)azetidine -2-carboxylic acid represented by the general formula (5') which has crystallized out in advance plays the roll of seed crystals, so that it is not necessary to especially add seed crystals. From the viewpoint of rate of crystallization, seed crystals are preferably added.

The seed crystals to be used are the same compound, the same optical isomer species as optically active N-(alkoxycarbonyl)azetidine-2-carboxylic acid to be obtained as-precipitate crystals. In cases where either one of the optical isomers is contained in a higher proportion in the optical isomer mixture, that optical isomer is generally obtained as precipitate crystals, so that crystals of that optical isomer occurring in a higher proportion are generally used as seed crystals. From the viewpoint of the optical purity of the optical isomer to be obtained as precipitate crystals, it is preferable that optically active N-(alkoxycarbonyl)azetidine-2-carboxylic acid to be used as seed crystals have an optical purity as high as possible, for example not less than 97% ee is preferred, more preferably not less than 98% ee.

The amount of the seed crystals of optically active N-(alkoxycarbonyl)azetidine-2-carboxylic acid to be added is not particularly restricted but, generally, it is not less than 0.0001% by weight, preferably not less than 0.0001% by weight but not more than 0.1% by weight, more preferably not less than 0.0001% by weight but not more than 0.08% by weight.

When crystals of optically active N-(alkoxycarbonyl) azetidine-2-carboxylic acid is added as seed crystals, the addition thereof may be made before cooling, during the process of cooling, or after cooling of the solution in which the optical isomer mixture is dissolved. For preventing the seed crystals added from being thoroughly dissolved in that solution after addition thereof, they are preferably added in the region of saturation or supersaturation of the optical isomer mixture. From the viewpoint of the optical purity of the optical isomer to be obtained as precipitate crystals, seed crystals are preferably added before the precipitate crystals crystallize out.

Therefore, the seed crystal addition is generally conducted at any time between just before the start of cooling and just after the stop of cooling, among this period, preferably during the period from the start of cooling to the stop of cooling. For example, crystals can be caused to precipitate out by cooling the solution of the optical isomer mixture of N-(alkoxycarbonyl)azetidine-2-carboxylic acid represented by the general formula (5') once to a temperature lower by 1 to 30° C. than the dissolution temperature, then adding seed crystals and further cooling the solution or maintaining the temperature at the addition as it is. From the viewpoint of yield, however, it is preferably to further cool the solution after seed crystal addition. The seed crystal addition is made generally once but, if necessary, may be made twice or more times.

Crystals of optically active N-(alkoxycarbonyl)azetidine-2-carboxylic acid precipitate out as mentioned above. From the viewpoint of yield, the solution is preferably allowed to stand for a while. The time of allowing to stand is not particularly restricted but, generally, it is within about 20 hours, preferably about 30 minutes to about 15 hours.

The thus-obtained crystallization product can easily be separated from the optical isomer mixture in the solution by a filtration procedure, for instance. Thus, N-(alkoxycarbonyl)azetidine-2-carboxylic acid represented by the general formula (5') can be obtained with a high optical purity, for example an optical purity of not less than 98% ee.

BEST MODES FOR CARRYING OUT THE INVENTION

The following examples illustrate the present invention in further detail. They are, however, by no means limitative of the scope of the present invention. The optical purity determination was carried out by high performance liquid chromatographic analysis.

EXAMPLE 1

[Compound (1)→(2)]

(S)-3-Hydroxy-2-pyrrolidinone (100.4 mg) was dissolved in 3 ml of dioxane, 248.4 mg of thionyl chloride was added, and the mixture was stirred at room temperature for 4 hours. Further, 3.0 mg of pyridine was added, and the mixture was stirred at 50° C. for 3 hours. After confirmation of disappearance of the starting material by TLC, the reaction solvent was distilled off under reduced pressure and, then, water and ethyl acetate were added. The aqueous layer was extracted five times with ethyl acetate. All the organic layers were combined and washed with a saturated aqueous solution of sodium chloride. After drying over sodium sulfate, the solvent was distilled off to give 92.0 mg of (R)-3-chloro-2-pyrrolidinone (yield 77.5%, optical purity 93.5% ee). For the analysis of the optical purity, high performance liquid chromatography using a chiral column (Chiralcel OB-H (Daicel)) was used.

$^1$H-NMR (D$_2$O) δ 2.35 (m, 1H), 2.74 (m, 1H), 3.46 (m, 1H), 3.54 (m, 1H), 4.58 (t, 1H)

$^{13}$C-NMR (D$_2$O) δ 34.2, 43.2, 58.0, 179.1 IR (KBr) 1700 cm$^{-1}$

EXAMPLE 2

[Compound (2)→(3)]

(R)-3-Chloro-2-pyrrolidinone (152.6 mg; optical purity 75.3% ee) was dissolved in 10 ml of 3.0 M sulfuric acid aqueous solution and the solution was stirred at 80° C. for 7 hours and then at 90° C. for 3 hours. This reaction solution was passed several times through an ion exchange resin (Amberlite IR 120) column and, then, the ion exchange resin was washed with water until the pH of washings reached to 6 to 7. Thereafter, the ion exchange resin was washed with aqueous ammonia, and the washings were concentrated to give 158 mg of (R)-4-amino-2-chlorobutyric acid (yield 90.1%).

$^1$H-NMR (D$_2$O) δ 2.15–2.45 (m, 2H), 3.19 (t, 2H), 4.45 (t, 1H)

$^{13}$C-NMR (D$_2$O) δ 35.6, 39.6, 61.7, 178.4

EXAMPLE 3

[Compound (2)→(3)→(4)]

(R)-3-Chloro-2-pyrrolidinone (114.5 mg; optical purity 75.3% ee) was dissolved in 7.5 ml of 3.0 M sulfuric acid aqueous solution and the solution was stirred at 50° C. for 18 hours, then at 80° C. for 5 hours and finally at 90° C. for 3 hours. Without particularly isolating (R)-4-amino-2-chlorobutyric acid in the reaction solution, the reaction solution was neutralized with a 30% sodium hydroxide aqueous solution until a pH of 11, 1.21 g of barium hydroxide octahydrate was added, and the solution was stirred with heating at 100° C. for 26 minutes. The reaction solution was adjusted to pH 1 by addition of 6 N hydrochloric acid. The reaction solution was passed several times through an ion exchange resin (Amberlite IR 120) column and, then, the ion exchange resin was washed with water until the pH of washings reached to 6 to 7. Thereafter, the ion exchange resin was washed with aqueous ammonia, and the washings were concentrated to give 70.8 mg of (S)-azetidine-2-carboxylic acid (yield 73.2%, optical purity 67.9% ee). The analysis of the optical purity was carried out by derivatizing the product into N-(tert-butoxycarbonyl)azetidine-2-carboxylic acid using di-tert-butyl dicarbonate, followed by high performance liquid chromatography using a chiral column (Chiralcel OD-R (Daicel)).

$^1$H-NMR (CD$_3$OD) δ 2.15 (m, 1H), 2.58 (m, 1H), 3.90 (m, 1H), 4.02 (q, 1H), 4.60 (t, 1H)

EXAMPLE 4

[Compound (2)→(3)→(4)→(5)]

(R)-3-Chloro-2-pyrrolidinone (76.3 mg; optical purity 75.3% ee) was dissolved in 5 ml of 3.0 M sulfuric acid aqueous solution and the solution was stirred at 50° C. for 18 hours, then at 80° C. for 5 hours and finally at 90° C. for 3 hours. Without particularly isolating (R)-4-amino-2-chlorobutyric acid in the reaction solution, the reaction solution was neutralized with a 30% sodium hydroxide aqueous solution until a pH of 11, 805.4 mg of barium hydroxide octahydrate was added, and the solution was stirred with heating at 100° C. for 26 minutes. Without particularly isolating (S)-azetidine-2-carboxylic acid in the reaction solution, 6 N hydrochloric acid was added to the reaction solution to bring pH to 9.8. Then, 275.5 mg of sodium carbonate and 278.5 mg of di-tert-butyl dicarbonate were added, and the solution was stirred at room temperature for 16 hours. This was adjusted to pH 1.9 by addition of 6 N hydrochloric acid and then extracted three times with ethyl acetate. The organic layer was washed with a saturated aqueous solution of sodium chloride and then dried over sodium sulfate, and the solvent was distilled off to give (S)-N-(tert-butoxycarbonyl)azetidine-2-carboxylic acid (yield 71.7%, optical purity 67.9% ee). The yield was determined by using high performance liquid chromatography using highly pure (S)-N-(tert-butoxycarbonyl)azetidine-2-carboxylic acid as a standard.

$^1$H-NMR (CDCl$_3$) δ 1.48 (s, 9H), 2.40–2.60 (bs, 2H), 3.80–4.00 (bs, 2H), 4.80 (t, 1H)

$^{13}$C-NMR (CDCl$_3$) δ 19.9, 28.3, 47.2, 60.4, 81.6, 157.3, 173.5

EXAMPLE 5

[Compound (2)→(3)→(4)→(5)]

(S)-3-Chloro-2-pyrrolidinone (10.1 mg; optical purity 93.3% ee) was dissolved in 4 ml of 6.0 M hydrochloric acid and the solution was stirred at 50° C. for 1 hour and then further at 80° C. for 3 hours. Without particularly isolating (S)-4-amino-2-chlorobutyric acid in the reaction solution, the reaction solution was neutralized with a 30% sodium hydroxide aqueous solution until a pH of 11, 110.8 mg of barium hydroxide octahydrate was added, and the solution was stirred with heating at 100° C. for 23 minutes. Without particularly isolating (R)-azetidine-2-carboxylic acid in the reaction solution, 6 N hydrochloric acid was added to the reaction solution to adjust pH to 9.1. Then, 71.4 mg of sodium carbonate and 49.3 mg of di-tert-butyl dicarbonate were added, and the mixture was stirred at room temperature for 14 hours. This was adjusted to pH 1.8 by addition of 6 N hydrochloric acid and then extracted three times with ethyl acetate. The organic layer was washed with a saturated aqueous solution of sodium chloride and then dried over sodium sulfate, and the solvent was distilled off to give 14.1 mg of (R)-N-(tert-butoxycarbonyl)azetidine-2-carboxylic acid (yield 82.0%, optical purity 52.8% ee).

EXAMPLE 6
[Compound (2)→(3)→(4)→(5)]

(R)-3-Chloro-2-pyrrolidinone (62.5 mg, optical purity 75.3% ee) was dissolved in 5 ml of water, 319.1 mg of barium hydroxide octahydrate was added, and the solution was stirred at room temperature for 16 hours. Without particularly isolating (R)-4-amino-2-chlorobutyric acid in the reaction solution, the mixture was further stirred at 100° C. for 30 minutes. Without particularly isolating (S)-azetidine-2-carboxylic acid in the reaction solution, 6 N hydrochloric acid was added to the reaction solution to adjust pH to 9.6, 224.3 mg of sodium carbonate and 233.1 mg of di-tert-butyl dicarbonate were added, and the mixture was stirred at room temperature for 10 hours. This was adjusted to pH 1.9 by addition of 6 N hydrochloric acid and then extracted three times with ethyl acetate. The organic layer was washed with a saturated aqueous solution of sodium chloride and then dried over sodium sulfate, and the solvent was distilled off to give (S)-N-(tert-butoxycarbonyl)azetidine-2-carboxylic acid (yield 71.8%, optical purity 27.6% ee). The yield was determined by high performance liquid chromatography using highly pure (S)-N-(tert-butoxycarbonyl)azetidine-2-carboxylic acid as a standard.

EXAMPLE 7
[Compound (2)→(3)→(4)→(5)]

(R)-3-Chloro-2-pyrrolidinone (7.63 g, optical purity 93.5% ee) was dissolved in 500 ml of 3.0 M sulfuric acid aqueous solution, and the solution was stirred at 50° C. for 10 hours, then at 80° C. for 5hours and finally at 90° for 3 hours. Without particularly isolating (R)-4-amino-2-chlorobutyric acid in the reaction solution, the solution was neutralized to pH 11 with a 30% sodium hydroxide aqueous solution, 80.54 g of barium hydroxide octahydrate was added, and the mixture was stirred with heating at 100° C. for 26 minutes. Without particularly isolating (S)-azetidine-2-carboxylic acid in the reaction solution, 6 N hydrochloric acid was added to the reaction solution to adjust pH to 9.8, 27.55 g of sodium carbonate and 27.85 g of di-tert-butyl dicarbonate were added, and the mixture was stirred at room temperature for 16 hours. This was adjusted to pH 1.9 by addition of 6 N hydrochloric acid and then extracted three times with ethyl acetate. The organic layer was washed with a saturated aqueous solution of sodium chloride and then dried over sodium sulfate, the solvent was distilled off, and the white solid thus obtained was recrystallized from ethyl acetate/hexane (1/1, w/w) to give 4.26 g of (S)-N-(tert-butoxycarbonyl)azetidine-2-carboxylic acid (yield 33.2%, optical purity 99.9% ee).

EXAMPLE 8
[Compound (6)→(7)]

To methyl (S)-4-amino-2-hydroxybutyrate hydrochloride (169.0 mg; 132.7 mg when calculated as methyl (S)-4-amino-2-hydroxybutyrate) was added 3 ml of dioxane, followed by further addition of 178.5 mg of thionyl chloride. The mixture was stirred at room temperature for 2 hours. Thereafter, 2.3 mg of pyridine was added, and the mixture was further stirred at 50° C. for 3 hours. After confirmation of disappearance of the starting material by TLC, the solvent was distilled off under reduced pressure to give 196. 8 mg of methyl (R)-4-amino-2-chlorobutyrate hydrochloride (yield quantitative, optical purity 93.9% ee). The analysis of the optical purity was carried out by derivatizing into (R)-3-chloro-2-pyrrolidinone with sodium hydrogen carbonate, followed by high performance liquid chromatography using a chiral column (Chiralcel OB-H (Daicel)).

$^1$H-NMR (D$_2$O) δ:; 2.35 (m, 1H), 2.48 (m, 1H), 3.24 (m, 2H), 3.85 (s, 3H), 4.74 (m, 1H)

EXAMPLE 9-1
[Compound (6)→(7)]

To methyl (S)-4-amino-2-hydroxybutyrate hydrochloride (170.1 mg; 133.5 mg when calculated as methyl (S)-4-amino-2-hydroxybutyrate) was added 3 ml of 4 N HCl/dioxane, followed by further addition of 189.1 mg of thionyl chloride. The mixture was stirred at room temperature for 1 hour. Thereafter, 2.5 mg of pyridine was added, and the mixture was further stirred at 50° C. for 6 hours. After confirmation of disappearance of the starting material by TLC, the solvent was distilled off under reduced pressure to give 191.6 mg of methyl (R)-4-amino-2-chlorobutyrate hydrochloride (yield quantitative, optical purity 93.9% ee). The analysis of the optical purity was carried out by derivatizing into (R)-3-chloro-2-pyrrolidinone with sodium hydrogen carbonate, followed by high performance liquid chromatography using a chiral column (Chiralcel OB-H (Daicel)).

$^1$H-NMR (D$_2$O) δ 2.35 (m, 1H), 2.48 (m, 1H), 3.24 (m, 2H), 3.85 (s, 3H), 4.74 (m, 1H)

EXAMPLE 9-2
[Compound (6)→(7)]

To methyl (S)-4-amino-2-hydroxybutyrate hydrochloride (498 mg; 391 mg when calculated as methyl (S)-4-amino-2-hydroxybutyrate) was added 5 ml of 4 N-HCl/dioxane, followed by further addition of 321 μL of thionyl chloride. The mixture was stirred at 50° C. for 4 hours. The solvent was distilled off under reduced pressure to give 530 mg of methyl (R)-4-amino-2-chlorobutyrate hydrochloride (yield quantitative, optical purity 98.5% ee). The analysis of the optical purity was carried out by derivatizing into (R)-3-chloro-2-pyrrolidinone with sodium hydrogen carbonate, followed by high performance liquid chromatography using a chiral column (Chiralcel OB-H (Daicel)).

EXAMPLE 9-3
[Compound (6)→(7)]

To methyl (S)-4-amino-2-hydroxybutyrate hydrochloride (521.6 mg; 409.5 mg when calculated as methyl (S)-4-amino-2-hydroxybutyrate) was added 1.8 mL of thionyl chloride. The mixture was stirred at room temperature for 3 hours and then at 50° C. for 4 hours. Thereafter, the solvent was distilled off under reduced pressure to give 576.2 mg of methyl (R)-4-amino-2-chlorobutyrate hydrochloride (yield quantitative, optical purity 96.9% ee). The analysis of the optical purity was carried out by derivatizing into (R)-3-chloro-2-pyrrolidinone with sodium hydrogen carbonate, followed by high performance liquid chromatography using a chiral column (Chiralcel OB-H (Daicel)).

EXAMPLE 10
[Compound (7)→(3)]

Methyl (R)-4-amino-2-chlorobutyrate hydrochloride (116.1 mg, optical purity 93.9% ee) was dissolved in 15 ml of 1.0 M sulfuric acid aqueous solution, and the solution was stirred at room temperature for 27 hours. This reaction solution was passed several times through an ion exchange resin (Amberlite IR 120) column and, then, the ion exchange resin was washed with water until pH of washings reached to 6 to 7. Thereafter, the ion exchange resin was washed with aqueous ammonia, and the washings were concentrated to give 75.9 mg of (R)-4-amino-2-chlorobutyric acid (yield 89.3%).

$^1$H-NMR (D$_2$O) δ 2.15–2.45 (m, 2H), 3.19 (t, 2H), 4.45 (t, 1H)

$^{13}$C-NMR (D$_2$O) δ 35.6, 39.6, 61.7, 178.4

EXAMPLE 11

[Compound (7)→(3)→(4)]

Methyl (R)-4-amino-2-chlorobutyrate hydrochloride (77.4 mg, optical purity 93.9% ee) was dissolved in 10 ml of 1.0 M sulfuric acid aqueous solution, and the solution was stirred at room temperature for 27 hours. Without particularly isolating (R)-4-amino-2-chlorobutyric acid in the reaction solution, the solution was neutralized to pH 7 with a 30% sodium hydroxide aqueous solution, 519.4 mg of barium hydroxide octahydrate was added, and the mixture was stirred with heating at 100° C. for 27 minutes. 6 N hydrochloric acid was added to the reaction solution to adjust pH to 1.0. This reaction solution was passed several times through an ion exchange resin (Amberlite IR 120) column and, then, the ion exchange resin was washed with water until the pH of washings reached to 6 to 7. Thereafter, the ion exchange resin was washed with aqueous ammonia, and the washings were concentrated to give 25.2 mg of (S)-azetidine-2-carboxylic acid (yield 60.5%, optical purity 87.0% ee). The analysis of the optical purity was carried out by derivatizing into N-(tert-butoxycarbonyl)azetidine-2-carboxylic acid with di-tert-butyl dicarbonate, followed by high performance liquid chromatography using a chiral column (Chiralcel OD-R (Daicel)).

$^1$H-NMR (CD$_3$OD) δ 2.15 (m, 1H), 2.58 (m, 1H), 3.90 (m, 1H), 4.02 (q, 1H), 4.60 (t, 1H)

EXAMPLE 12

[Compound (7)→(3)→(4)→(5)]

Methyl (R)-4-amino-2-chlorobutyrate hydrochloride (38.7 mg, optical purity 93.9% ee) was dissolved in 5 ml of 1.0 M sulfuric acid aqueous solution, and the solution was stirred at room temperature for 27 hours. Without particularly isolating (R)-4-amino-2-chlorobutyric acid in the reaction solution, the reaction solution was neutralized to pH 7 with a 30% sodium hydroxide aqueous solution, 259.7 mg of barium hydroxide octahydrate was added, and the solution was stirred with heating at 100° C. for 27 minutes. Without particularly isolating (S)-azetidine-2-carboxylic acid in the reaction solution, 6 N hydrochloric acid was added to the reaction solution to adjust pH to 9.4, 94.1 mg of sodium carbonate and 93.6 mg of di-tert-butyl dicarbonate were added, and the solution was stirred at room temperature for 19 hours. This was adjusted to pH 1.8 by addition of 6 N hydrochloric acid, and extracted three times with ethyl acetate. The organic layer was washed with a saturated aqueous solution of sodium chloride and dried over sodium sulfate, and the solvent was distilled off to give (S)-N-(tert-butoxycarbonyl)azetidine-2-carboxylic acid (yield 61.8%, optical purity 87.0% ee). The yield was determined by high performance liquid chromatography using highly pure (S)-N-(tert-butoxycarbonyl)azetidine-2-carboxylic acid as a standard. The analysis of the optical purity was carried out by high performance liquid chromatography using a chiral column (Chiralcel OD-R (Daicel)).

$^1$H-NMR (CDCl$_3$) δ 1.48 (s, 9H), 2.40–2.60 (bs, 2H), 3.80–4.00 (bs, 2H), 4.80 (t, 1H)

$^{13}$C-NMR (CDCl$_3$) δ 19.9, 28.3, 47.2, 60.4, 81.6, 157.3, 173.5

EXAMPLE 13

[Compound (6)→(7)→(2)]

To methyl (S)-4-amino-2-hydroxybutyrate hydrochloride (169.0 mg; 132.7 mg when calculated as methyl (S)-4-amino-2-hydroxybutyrate) was added 3 ml of dioxane, followed by further addition of 178.5 mg of thionyl chloride. The mixture was stirred at room temperature for 2 hours. Thereafter, 2.3 mg of pyridine was added, and the mixture was further stirred at 50° C. for 3 hours. After confirmation of disappearance of the starting material by TLC, the solvent was distilled off under reduced pressure to give methyl (R)-4-amino-2-chlorobutyrate hydrochloride. To this were added 10 ml of chloroform and 5 ml of a saturated aqueous solution of sodium hydrogen carbonate, and the aqueous layer was further extracted six times with chloroform. The organic layer was dried over sodium sulfate and the solvent was distilled off to give 125.5 mg of (R)-3-chloro-2-pyrrolidinone (yield quantitative, optical purity 93.9% ee). The analysis of the optical purity was carried out by high performance liquid chromatography using a chiral column (Chiralcel OB-H (Daicel))

$^1$H-NMR (D$_2$O) δ 2.35 (m, 1H), 2.74 (m, 1H), 3.46 (m, 1H), 3.54 (m, 1H), 4.58 (t, 1H)

$^{13}$C-NMR (D$_2$O) δ 34.2, 43.2, 58.0, 179.1 IR (KBr) 1700 cm$^{-1}$

EXAMPLE 14

[Compound (6)→(7)→(2)]

To methyl (S)-4-amino-2-hydroxybutyrate hydrochloride (170.1 mg; 133.5 mg when calculated as methyl (S)-4-amino-2-hydroxybutyrate) was added 3 ml of 4 N-HCl/dioxane, followed by further addition of 189.1 mg of thionyl chloride. The mixture was stirred at room temperature for 1 hour. Thereafter, 2.5 mg of pyridine was added, and the mixture was further stirred at 50° C. for 6 hours. After confirmation of disappearance of the starting material by TLC, the solvent was distilled off under reduced pressure to give methyl (R)-4-amino-2-chlorobutyrate hydrochloride. To this were added 10 ml of chloroform and 5 ml of a saturated aqueous solution of sodium hydrogen carbonate, and the aqueous layer was further extracted six times with chloroform. The organic layer was dried over sodium sulfate and the solvent was distilled off to give 120.7 mg of (R)-3-chloro-2-pyrrolidinone (yield quantitative, optical purity 93.9% ee). The optical purity was determined by high performance liquid chromatography using a chiral column (Chiralcel OB-H (Daicel)).

$^1$H-NMR (D$_2$O) δ 2.35 (m, 1H), 2.74 (m, 1H), 3.46 (m, 1H), 3.54 (m, 1H), 4.58 (t, 1H)

$^{13}$C-NMR (D$_2$O) δ 34.2, 43.2, 58.0, 179.1 IR (KBr) 1700 cm$^{-1}$

EXAMPLE 15

[Recrystallization of Compound (5)]

N-(tert-Butoxycarbonyl)azetidine-2-carboxylic acid (5.30 g; L form 85.8% ee) was dissolved in 13.02 g of ethyl acetate, followed by addition of 11.94 g of hexane to thereby attain complete dissolution at 50° C. The temperature of this solution was lowered to 25° C. at a rate of 25° C./hour, 1.0 mg of L-N-(tert-butoxycarbonyl)azetidine-2-carboxylic acid (optical purity at least 99.9% ee) was added as seed crystals, and the mixture was stirred at the same temperature for 13 hours. The resulting white crystals were colleted by filtration, whereupon 2.45 g of L-N-(tert-butoxycarbonyl) azetidine-2-carboxylic acid was obtained as a first crop (L form, optical purity at least 99.9% ee, recovery 46.2% based on the optical isomer mixture of N-(tert-butoxycarbonyl) azetidine-2-carboxylic acid).

Then, the solvent was distilled off from the above filtrate, the thus-recovered N-(tert-butoxycarbonyl)azetidine-2-carboxylic acid (2.85 g, L-form 73.2% ee) was dissolved in 6.99 g of ethyl acetate, and 6.54 g of hexane was added thereto to thereby attain complete dissolution at 50° C. The temperature of this solution was lowered to 25° C. at a rate of 25° C./hour, 0.9 mg of L-N-(tert-butoxycarbonyl) azetidine-2-carboxylic acid (optical purity at least 99.9% ee)

was added as seed crystals, and the mixture was stirred at the same temperature for 4 hours and then cooled to 0° C. at the same rate of cooling and further stirred at 0° C. for 3 hours. The resulting white crystals were collected by filtration, whereupon 1.32 g of L-N-(tert-butoxycarbonyl)azetidine-2-carboxylic acid was obtained as a second crop [L form, optical purity at least 99.9% ee, recovery 46.3% based on the optical isomer mixture of N-(tert-butoxycarbonyl)azetidine-2-carboxylic acid].

Thus was obtained 3.77 g, as the sum of the first and second crops, of L-N-(tert-butoxycarbonyl)azetidine-2-carboxylic acid [recovery rate 71.1% based on the optical isomer mixture of N-(tert-butoxycarbonyl)azetidine-2-carboxylic acid].

EXAMPLE 16
[Recrystallization of Compound (5)]

To 2.69 g of N-(tert-butoxycarbonyl)azetidine-2-carboxylic acid (L form, 82.6% ee) was added 9.75 g of toluene to thereby attain complete dissolution at 40° C. The temperature of this solution was lowered to 25° C. at a rate of 25° C./hour, 1.0 mg of L-N-(tert-butoxycarbonyl)azetidine-2-carboxylic acid (optical purity at least 99.9% ee) was added as seed crystals, and the mixture was stirred at the same temperature for 2 hours. The temperature was then further lowered to 0° C. at the same rate of cooling, and the mixture was stirred at 0° C. for 2 hours. The resulting white crystals were colleted by filtration, whereupon 1.68 g of L-N-(tert-butoxycarbonyl)azetidine-2-carboxylic acid was obtained [L form, optical purity at least 99.9% ee, recovery 62.5% based on the optical isomer mixture of N-(tert-butoxycarbonyl)azetidine-2-carboxylic acid].

EXAMPLE 17
[Recrystallization of Compound (5)]

N-(tert-Butoxycarbonyl)azetidine-2-carboxylic acid (2.61 g; L form 82.6% ee) was dissolved in 7.44 g of tert-butyl methyl ether, followed by addition of 4.89 g of hexane to thereby attain complete dissolution at 40° C. The temperature of this solution was lowered to 25° C. at a rate of 25° C./hour, and the solution was stirred at the same temperature for 6 hours. The resulting white crystals were colleted by filtration, whereupon 1.45 g of L-N-(tert-butoxycarbonyl)azetidine-2-carboxylic acid was obtained [L form, optical purity at least 99.9% ee, recovery 55.6% based on the optical isomer mixture of N-(tert-butoxycarbonyl)azetidine-2-carboxylic acid].

EXAMPLE 18
[Recrystallization of Compound (5)]

N-(tert-Butoxycarbonyl)azetidine-2-carboxylic acid (2.61 g; L form 82.6% ee) was dissolved in 3.38 g of ethyl acetate, followed by addition of 6.26 g of toluene to thereby attain complete dissolution at 50° C. The temperature of this solution was lowered to 25° C. at a rate of 25° C./hour, 1.2 mg of L-N-(tert-butoxycarbonyl)azetidine-2-carboxylic acid (optical purity at least 99.9% ee) was added as seed crystals, and the solution was stirred at the same temperature for 14 hours. The temperature was then further lowered to 0° C. at the same rate of cooling, and the solution was stirred at 0° C. for 7 hours. The resulting white crystals were colleted by filtration, whereupon 0.93 g of L-N-(tert-butoxycarbonyl)azetidine-2-carboxylic acid was obtained [L form, optical purity at least 99.9% ee, recovery 35.6% based on the optical isomer mixture of N-(tert-butoxycarbonyl)azetidine-2-carboxylic acid].

EXAMPLE 19
[Recrystallization of Compound (5)]

N-(tert-Butoxycarbonyl)azetidine-2-carboxylic acid (2.69 g; L form 82.6%ee) was dissolved in 0.90 g of acetonitrile, followed by addition of 1.72 g of toluene to thereby attain complete dissolution at 40° C. The temperature of this solution was lowered to 25° C. at a rate of 25° C./hour, 1.4 mg of L-N-(tert-butoxycarbonyl)azetidine-2-carboxylic acid (optical purity at least 99.9% ee) was added as seed crystals, and the solution was stirred at the same temperature for 3 hours. The resulting white crystals were colleted by filtration, whereupon 0.50 g of L-N-(tert-butoxycarbonyl)azetidine-2-carboxylic acid was obtained [L form, optical purity at least 99.9% ee, recovery 18.6% based on the optical isomer mixture of N-(tert-butoxycarbonyl)azetidine-2-carboxylic acid].

EXAMPLE 20
[Recrystallization of Compound (5)]

N-(tert-Butoxycarbonyl)azetidine-2-carboxylic acid (2.65 g; D form 85.8% ee) was dissolved in 6.51 g of ethyl acetate, followed by addition of 5.97 g of hexane to thereby attain complete dissolution at 50° C. The temperature of this solution was lowered to 25° C. at a rate of 25° C./hour, 0.5 mg of D-N-(tert-butoxycarbonyl)azetidine-2-carboxylic acid (optical purity at least 99.9% ee) was added as seed crystals, and the mixture was stirred at the same temperature for 13 hours. The resulting white crystals were colleted by filtration, whereupon 1.23 g of D-N-(tert-butoxycarbonyl)azetidine-2-carboxylic acid was obtained [D form, optical purity at least 99.9% ee, recovery 46.2% based on the optical isomer mixture of N-(tert-butoxycarbonyl)azetidine-2-carboxylic acid].

INDUSTRIAL APPLICABILITY

The production methods according to the invention, which are constituted as mentioned above, can give an optically active azetidine-2-carboxylic acid from an optically active 3-hydroxy-2-pyrrolidinone or from an optically active 4-amino-2-hydroxybutyric acid ester in an efficient, simple and industrially advantageous manner.

Further, according to the method for obtaining according to the invention, an optically active N-(alkoxycarbonyl)azetidine-2-carboxylic acid can be recovered from a mixture of optical isomers of the N-(alkoxycarbonyl)azetidine-2-carboxylic acid in one step without using any expensive optical dissolution agent. Furthermore, the optically active N-(alkoxycarbonyl)azetidine-2-carboxylic acid recovered can have an optical purity of at least 99% ee.

What is claimed is:

1. A production method of an optically active 3-halo-2-pyrrolidinone represented by the general formula (2):

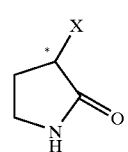

(2)

in the formula, X represents a halogen atom and * represents an asymmetric carbon atom, which comprises halogenating an optically active 3-hydroxy-2-pyrrolidinone represented by the general formula (1):

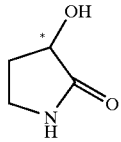
(1)

in the formula, * represents an asymmetric carbon atom, with inversion of configuration.

2. A production method of an optically active 4-amino-2-halobutyric acid represented by the general formula (3):

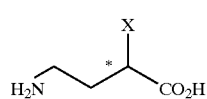
(3)

in the formula, X represents a halogen atom and * represents an asymmetric carbon atom, which comprises hydrolyzing an optically active 3-halo-2-pyrrolidinone represented by the general formula (2):

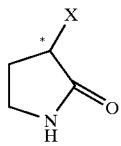
(2)

in the formula, X represents a halogen atom and * represents an asymmetric carbon atom.

3. A production method of an optically active 4-amino-2-halobutyric acid represented by the general formula (3):

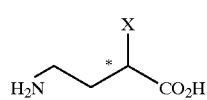
(3)

in the formula, X represents a halogen atom and * represents an asymmetric carbon atom, which comprises halogenating an optically active 3-hydroxy-2-pyrrolidinone represented by the general formula (1):

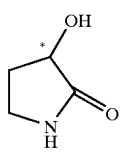
(1)

in the formula, * represents an asymmetric carbon atom, with inversion of configuration to prepare an optically active 3-halo-2-pyrrolidinone represented by the general formula (2):

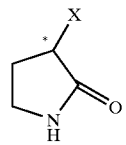
(2)

in the formula, X represents a halogen atom and * represents an asymmetric carbon atom, followed by hydrolysis.

4. A production method of an optically active azetidine-2-carboxylic acid represented by the general formula (4):

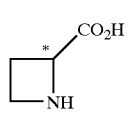
(4)

in the formula, * represents an asymmetric carbon atom, which comprises halogenating an optically active 3-hydroxy-2-pyrrolidinone represented by the general formula (1):

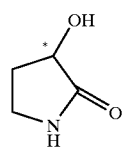
(1)

in the formula, * represents an asymmetric carbon atom, with inversion of configuration to prepare an optically active 3-halo-2-pyrrolidinone represented by the general formula (2):

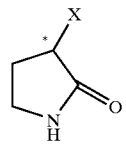
(2)

in the formula, X represents a halogen atom and * represents an asymmetric carbon atom, hydrolyzing the same to prepare an optically active 4-amino-2-halobutyric acid represented by the general formula (3):

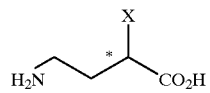
(3)

in the formula, X represents a halogen atom and * represents an asymmetric carbon atom, followed by cyclizing the reaction product in an alkaline aqueous solution.

5. A production method of an optically active N-protected azetidine-2-carboxylic acid represented by the general formula (5):

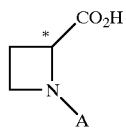
(5)

in the formula, A represents an amino group-protecting group and * represents an asymmetric carbon atom,
which comprises halogenating an optically active 3-hydroxy-2-pyrrolidinone represented by the general formula (1):

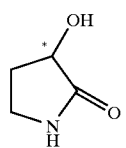
(1)

in the formula, * represents an asymmetric carbon atom, with inversion of configuration to prepare an optically active 3-halo-pyrrolidinone represented by the general formula (2):

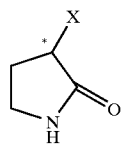
(2)

in the formula, X represents a halogen atom and * represents an asymmetric carbon atom,
hydrolyzing the same to prepare an optically active 4-amino-2-halobutyric acid represented by the general formula (3):

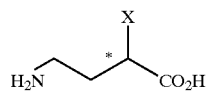
(3)

in the formula, X represents a halogen atom and * represents an asymmetric carbon atom,
cyclizing the reaction product in an alkaline aqueous solution to prepare an optically active azetidine-2-carboxylic acid represented by the general formula (4):

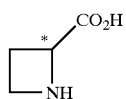
(4)

in the formula, * represents an asymmetric carbon atom,
followed by treating the reaction product with an amino group-protecting agent.

6. The production method according to claim 5,
wherein the optical purity of the optically active N-protected azetidine-2-carboxylic acid obtained is improved by carrying out recrystallization thereof.

7. The production method according to claim 5,
wherein the amino group-protecting group A is an alkoxycarbonyl group.

8. The production method according to claim 7,
wherein the alkoxycarbonyl group is a tert-butoxycarbonyl group.

9. The production method according to claim 2,
wherein the hydrolysis of the optically active 3-halo-2-pyrrolidinone (2) is carried out in an acidic aqueous solution.

10. The production method according to claim 9,
wherein the acidic aqueous solution is a sulfuric acid aqueous solution.

11. The production method according to claim 1,
wherein thionyl chloride is used as a halogenating agent for the halogenation.

12. The production method according to claim 1,
wherein one species selected from the group consisting of dioxane, tetrahydrofuran, ethylene glycol dimethyl ether and thionyl chloride is used as a reaction solvent for the halogenation.

13. The production method according to claim 1,
wherein a tertiary amine or N,N-dimethylformamide is used as a catalyst for the halogenation.

14. The production method according to claim 1,
wherein the halogen atom X is a chlorine or a bromine.

15. An optically active 3-halo-2-pyrrolidinone represented by the general formula (2):

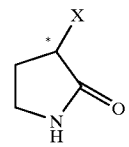
(2)

in the formula, X represents a halogen atom and * represents an asymmetric carbon atom.

16. The compound according to claim 15,
wherein the halogen atom X is a chlorine.

17. The production method of an optically active 3-halo-2-pyrrolidinone represented by the general formula (2):

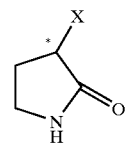
(2)

in the formula, X represents a halogen atom and * represents an asymmetric carbon atom,
which comprises cyclizing an optically active 4-amino-2-halobutyric acid ester represented by the general formula (7):

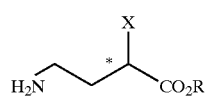
(7)

in the formula, R represents an ester type protective group, X represents a halogen atom and * represents an asymmetric carbon atom.

18. A production method of an optically active 3-halo-2-pyrrolidinone represented by the general formula (2):

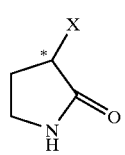
(2)

in the formula, X represents a halogen atom and * represents an asymmetric carbon atom, which comprises halogenating an optically active 4-amino-2-hydroxybutyric acid ester represented by the general formula (6):

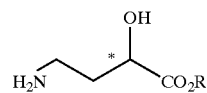
(6)

in the formula, R represents an ester type protective group and * represents an asymmetric carbon atom, with inversion of configuration to prepare an optically active 4-amino-2-halobutyric acid ester represented by the general formula (7):

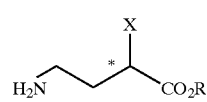
(7)

in the formula, R represents an ester type protective group, X represents a halogen atom and * represents an asymmetric carbon atom, followed by cyclization.

19. A production method of an optically active 4-amino-2-halobutyric acid represented by the general formula (3):

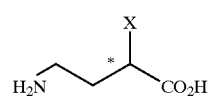
(3)

in the formula, X represents a halogen atom and * represents an asymmetric carbon atom, which comprises halogenating an optically active 4-amino-2-hydroxybutyric acid ester represented by the general formula (6):

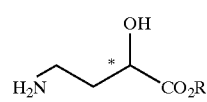
(6)

in the formula, R represents an ester type protective group and * represents an asymmetric carbon atom, with inversion of configuration to prepare an optically active 4-amino-2-halobutyric acid ester represented by the general formula (7):

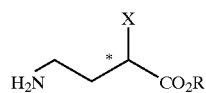
(7)

in the formula, R represents an ester type protective group, X represents a halogen atom and * represents an asymmetric carbon atom, cyclizing the same to prepare an optically active 3-halo-2-pyrrolidinone represented by the general formula (2):

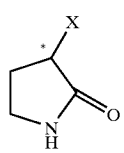
(2)

in the formula, X represents a halogen atom and * represents an asymmetric carbon atom, followed by hydrolysis.

20. A production method of an optically active azetidine-2-carboxylic acid represented by the general formula (4):

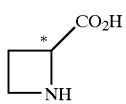
(4)

in the formula, * represents an asymmetric carbon atom, which comprises halogenating an optically active 4-amino-2-hydroxybutyric acid ester represented by the general formula (6):

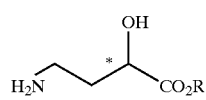
(6)

in the formula, R represents an ester type protective group and * represents an asymmetric carbon atom, with inversion of configuration to prepare an optically active 4-amino-2-halobutyric acid ester represented by the general formula (7):

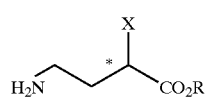
(7)

in the formula, R represents an ester type protective group, X represents a halogen atom and * represents an asymmetric carbon atom, cyclizing the same to prepare an optically active 3-halo-2-pyrrolidinone represented by the general formula (2):

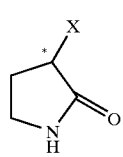
(2)

in the formula, X represents a halogen atom and * represents an asymmetric carbon atom, hydrolyzing the reaction product to prepare an optically active 4-amino-2-halobutyric acid represented by the general formula (3):

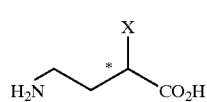
(3)

in the formula, X represents a halogen atom and * represents an asymmetric carbon atom, followed by cyclizing the reaction product in an alkaline aqueous solution.

21. A production method of an optically active N-protected azetidine-2-carboxylic acid represented by the general formula (5):

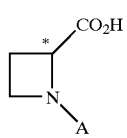
(5)

in the formula, A represents an amino-protecting group and * represents an asymmetric carbon atom, which comprises halogenating an optically active 4-amino-2-hydroxybutyric acid ester represented by the general formula (6):

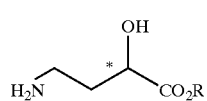
(6)

in the formula, R represents an ester type protective group and * represents an asymmetric carbon atom, with inversion of configuration to prepare an optically active 4-amino-2-halobutyric acid ester represented by the general formula (7):

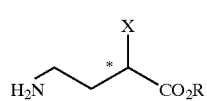
(7)

in the formula, R represents an ester type protective group, X represents a halogen atom and * represents an asymmetric carbon atom, cyclizing the same to prepare an optically active 3-halo-2-pyrrolidinone represented by the general formula (2):

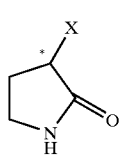
(2)

in the formula, X represents a halogen atom and * represents an asymmetric carbon atom, hydrolyzing the reaction product to prepare an optically active 4-amino-2-halobutyric acid represented by the general formula (3):

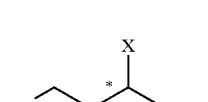
(3)

in the formula, X represents a halogen atom and * represents an asymmetric carbon atom, cyclizing the reaction product in an alkaline aqueous solution to prepare an optically active azetidine-2-carboxylic acid represented by the general formula (4):

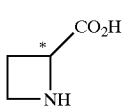
(4)

in the formula, * represents an asymmetric carbon atom, followed by treating the reaction product with an amino group-protecting agent.

22. The production method according to claim 21,
wherein the optical purity of the optically active N-protected azetidine-2-carboxylic acid (5) obtained is improved by carrying out recrystallization thereof.

23. The production method according to claim 21,
wherein the amino group protecting group A is an alkoxycarbonyl group.

24. The production method according to claim 23,
wherein the alkoxycarbonyl group is a tert-butoxycarbonyl group.

25. The production method according to claim 19,
wherein the hydrolysis of the optically active 3-halo-2-pyrrolidinone (2) is carried out in an acidic aqueous solution.

26. The production method according to claim 25,
wherein the acidic aqueous solution is a sulfuric acid aqueous solution.

27. The production method according to claim 18,
wherein thionyl chloride is used as a halogenating agent for the halogenation.

28. The production method according to claim 18,
wherein one species selected from the group consisting of dioxane, tetrahydrofuran, ethylene glycol dimethyl ether and thionyl chloride is used as a reaction solvent for the halogenation.

29. The production method according to claim 18, wherein a tertiary amine or N,N-dimethylformamide is used as a catalyst for the halogenation.

30. The production method according to claim 18, wherein the halogenation reaction is carried out in the presence of hydrogen chloride.

31. The production method according to claim 17, wherein the halogen atom X is a chlorine or a bromine.

32. The production method according to claim 17, wherein the ester type protective group R is an alkyl group containing 1 to 10 carbon atoms or an aralkyl group containing 7 to 10 carbon atoms.

* * * * *